US012616461B2

(12) United States Patent    (10) Patent No.:   US 12,616,461 B2
Hasan et al.      (45) Date of Patent:     May 5, 2026

(54) METHOD OF SUTURING A PROSTHETIC TO HUMAN TISSUE

(71) Applicant: Surgimatix, Inc., Elk Grove Village, IL (US)

(72) Inventors: Jafar Hasan, Oak Brook, IL (US);
Michael J. Shoup, Anoka, MN (US);
David Schaller, Chicago, IL (US);
Jane Kiernan, Chicago, IL (US);
Karen Noblett, Orange, CA (US);
Daniel Capua, Orland Park, IL (US);
Adam Saban, Sioux Falls, SD (US)

(73) Assignee: Surgimatix, Inc., Mansfield, MA (US)

( * ) Notice: Subject to any disclaimer, the term of this patent is extended or adjusted under 35 U.S.C. 154(b) by 0 days.

(21) Appl. No.: 18/224,425

(22) Filed: Jul. 20, 2023

(65) Prior Publication Data

US 2025/0025152 A1     Jan. 23, 2025

(51) Int. Cl.
*A61B 17/04*     (2006.01)
*A61F 2/00*     (2006.01)
*A61F 2/46*     (2006.01)

(52) U.S. Cl.
CPC .......... *A61B 17/0469* (2013.01); *A61B 17/04* (2013.01); *A61F 2/0004* (2013.01); *A61F 2/0045* (2013.01); *A61F 2/46* (2013.01); *A61B 2017/0496* (2013.01); *A61F 2/0036* (2013.01); *A61F 2/0063* (2013.01); *A61F 2220/0075* (2013.01)

(58) Field of Classification Search
CPC ... A61F 2/0004; A61F 2/0045; A61B 17/0469
See application file for complete search history.

(56) References Cited

U.S. PATENT DOCUMENTS

| | | | |
|---|---|---|---|
| 9,603,592 B2 | 3/2017 | Chin et al. | |
| 10,492,778 B2 | 12/2019 | Chin et al. | |
| 2011/0105836 A1* | 5/2011 | Miller | A61F 2/0063 600/37 |
| 2014/0257028 A1* | 9/2014 | Chu | A61F 2/0045 600/37 |

FOREIGN PATENT DOCUMENTS

| | | | | |
|---|---|---|---|---|
| WO | WO 2009/075932 | * | 6/2009 | A61F 2/0045 |

* cited by examiner

*Primary Examiner* — Carrie R Dorna
(74) *Attorney, Agent, or Firm* — von Briesen & Roper, s.c.

(57)      ABSTRACT
A method of side-suturing a prosthetic to human tissue is disclosed. The method includes accessing a surgical site on a body portion of a patient; identifying the human tissue within the surgical site; endomechanically positioning the prosthetic adjacent the human tissue within the surgical site; aligning a surgical tool proximate the tissue with the prosthetic between the tool and the tissue, the surgical tool having an elongated member with distal and proximal ends; actuating the surgical tool in-situ to drive deployment members of the surgical tool outwardly away from the surgical tool, through the prosthetic and into the tissue; and retracting the deployment members back into the surgical tool, whereby the deployment members deploy a fastener to fixatedly suspend the prosthetic to the human tissue.

14 Claims, 7 Drawing Sheets

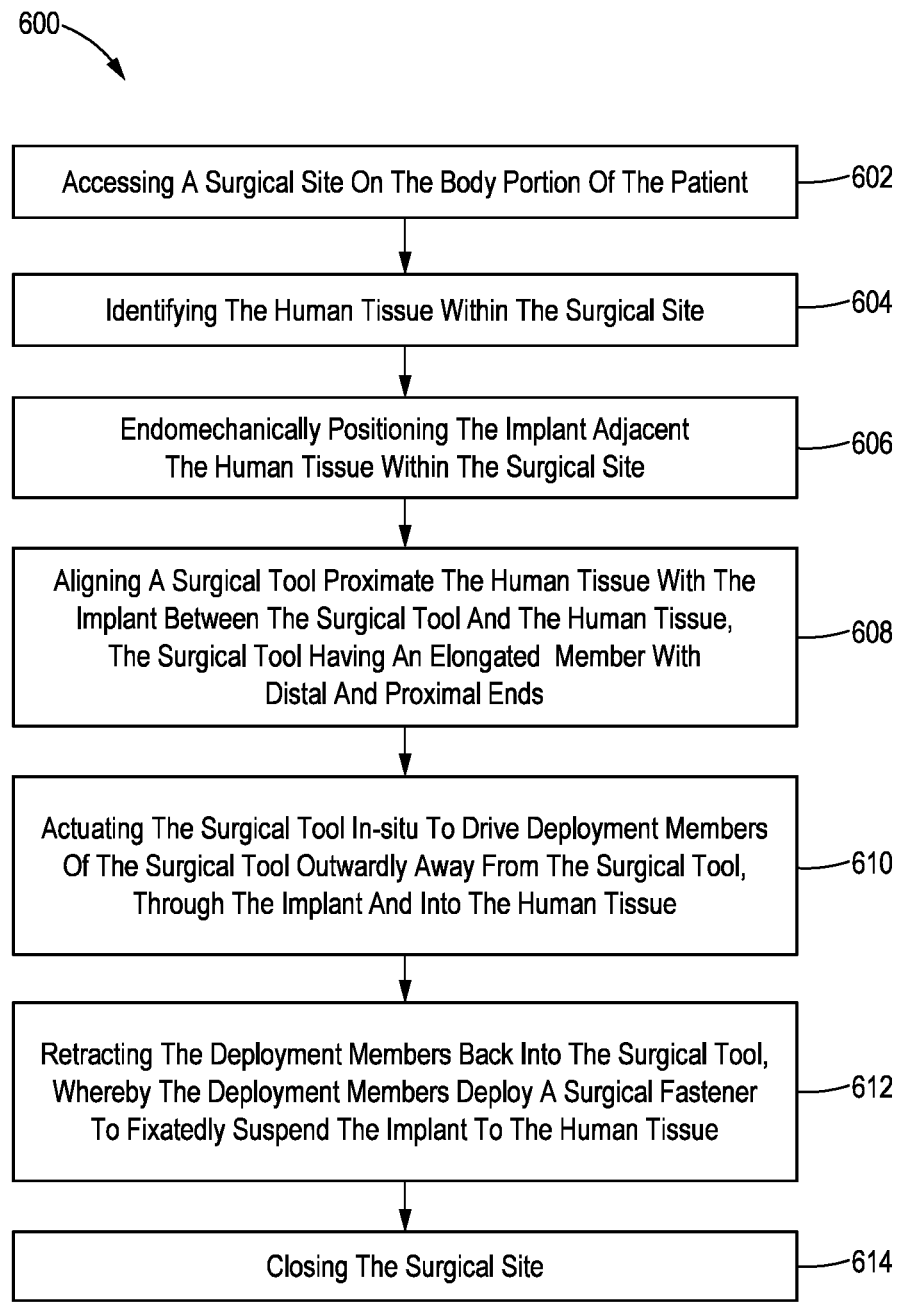

600

| Accessing A Surgical Site On The Body Portion Of The Patient | —602 |

| Identifying The Human Tissue Within The Surgical Site | —604 |

| Endomechanically Positioning The Implant Adjacent The Human Tissue Within The Surgical Site | —606 |

| Aligning A Surgical Tool Proximate The Human Tissue With The Implant Between The Surgical Tool And The Human Tissue, The Surgical Tool Having An Elongated Member With Distal And Proximal Ends | —608 |

| Actuating The Surgical Tool In-situ To Drive Deployment Members Of The Surgical Tool Outwardly Away From The Surgical Tool, Through The Implant And Into The Human Tissue | —610 |

| Retracting The Deployment Members Back Into The Surgical Tool, Whereby The Deployment Members Deploy A Surgical Fastener To Fixatedly Suspend The Implant To The Human Tissue | —612 |

| Closing The Surgical Site | —614 |

Accessing The Pelvic Cavity Of The Patient —702

Identifying The Prolapsed Organ Within The Pelvic Cavity —704

Positioning The Prolapsed Organ Proximate To A Human Tissue —706

Suturing, Via A Suturing Device, The Prolapsed Organ To The Human Tissue to Suspend the Prolapsed Organ Within the Pelvic Cavity —708

Closing Access To The Pelvic Cavity —710

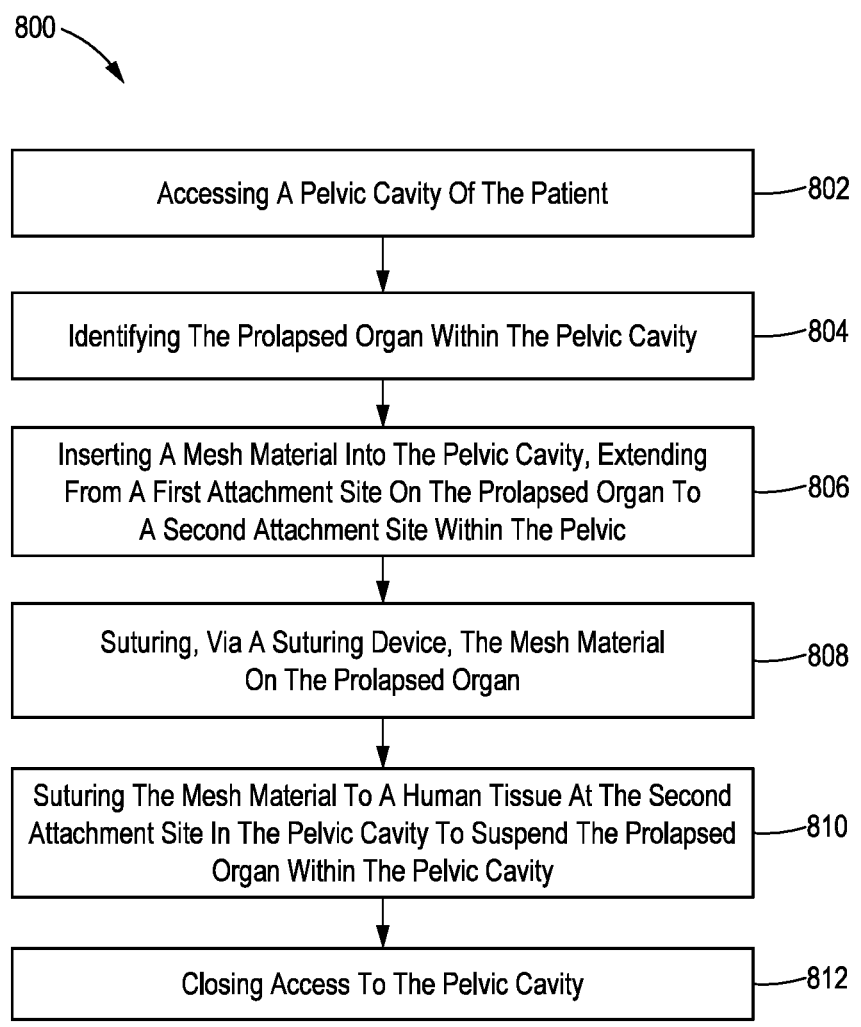

800

| Accessing A Pelvic Cavity Of The Patient | 802 |

| Identifying The Prolapsed Organ Within The Pelvic Cavity | 804 |

| Inserting A Mesh Material Into The Pelvic Cavity, Extending From A First Attachment Site On The Prolapsed Organ To A Second Attachment Site Within The Pelvic | 806 |

| Suturing, Via A Suturing Device, The Mesh Material On The Prolapsed Organ | 808 |

| Suturing The Mesh Material To A Human Tissue At The Second Attachment Site In The Pelvic Cavity To Suspend The Prolapsed Organ Within The Pelvic Cavity | 810 |

| Closing Access To The Pelvic Cavity | 812 |

*FIG. 8*

METHOD OF SUTURING A PROSTHETIC TO HUMAN TISSUE

TECHNICAL FIELD

The present disclosure relates to the field of surgical methods, and more particularly relates to surgical methods of suturing prosthetics to human tissue.

BACKGROUND

Pelvic organ prolapse is a prevalent condition affecting women, whereby organs such as the uterus, bladder, or rectum begin to descend or protrude in the pelvic cavity. Pelvic organ prolapse occurs when the muscles and human tissues that support the pelvic organs become weak or damaged. Healthy pelvic organs are supported by a pelvic floor and ligaments from the vagina to the backbone.

Human tissue refers to living or non-living biological material derived from the human body, including cells, organs, or anatomical structures. Prosthetic, as described herein, refer to artificial devices or materials designed to be surgically secured by a suture, fastener, or staple within the body to replace, support, or enhance the function of a specific organ, tissue, or body part. A suture is a thread-like material used by surgeons to stitch or secure tissues together during a surgical procedure for the purpose of attaching prosthetics, wound closure, and/or tissue approximation. A fastener may be used by surgeons to secure tissues together during a surgical procedure for the purpose of wound closure or tissue approximation. Organs are distinct anatomical structures composed of specialized human tissues that perform specific functions within the body, such as the heart, lungs, liver, or kidneys.

When the pelvic floor becomes stretched, weakened, damaged, or torn, it allows pelvic organs to slip out of their normal places or sag down as the ligaments will stretch over time causing pelvic organ prolapse. Different types of prolapse may occur, depending on the organ or organs involved. These may include uterine prolapse, vaginal prolapse, cystocele, rectocele, and enterocele. In uterine prolapse, the uterus and cervix drop down the vaginal canal potentially past the vaginal opening. Vaginal prolapse occurs when the top of the vagina drops down the vaginal canal, common with people who have had a hysterectomy (removal of their uterus). Cystocele occurs when the bladder bulges into the vagina. Rectocele occurs when the rectum bulges into the vagina. Enterocele occurs when the small intestine bulges against the vaginal wall.

Sacrocolpopexy is a surgical procedure commonly used to address pelvic organ prolapse. It involves attaching a mesh material as a prosthetic between the sacrum and the vaginal wall to provide support to the prolapsed organs. The mesh material may initially be attached by passing a suture or needle separately through the mesh material and a human tissue (i.e. vaginal wall), or vice versa. The mesh material may also be subsequently secured using in-situ suturing techniques. In-situ suturing refers to the suturing of tissues while they remain in their natural anatomical position or location within the body. During the sacrocolpopexy surgery, a surgeon lifts the affected organs back into place and secures them with a surgical mesh material. Restoring pelvic organs to their normal position helps relieve side effects of prolapse like bulging, pelvic pressure, or urinary incontinence (leaking urine).

Generally, surgeons perform sacrocolpopexy laparoscopically using small incisions and a camera. Some surgeons perform laparoscopic sacrocolpopexy with the aid of a robot. However, existing methods of surgery for suturing prolapsed organs present certain difficulties and limitations including a limited visibility of the surgical site, tissue handling, manual dexterity, and variabilities in anatomy of the patient.

Hence, there exists a need for improving surgical attachment of prosthetics to human tissue that provides durable support to the prolapsed organs in a minimally invasive approach for improved patient outcomes.

SUMMARY

In accordance with one aspect of the disclosure, a method of suturing a prosthetic to human tissue is disclosed. The method comprises: accessing a surgical site on a body portion of a patient; identifying the human tissue within the surgical site; endomechanically positioning the prosthetic adjacent the human tissue within the surgical site; aligning a surgical tool proximate the human tissue with the prosthetic between the tool and the human tissue, the surgical tool having an elongated member with distal and proximal ends and a lateral side therebetween; actuating the surgical tool in-situ to drive deployment members of the surgical tool outwardly away from the lateral side, through the prosthetic and into the tissue; and retracting the deployment members back into the lateral side of the surgical tool leaving the prosthetic suspended from the tissue.

In accordance with another aspect of the disclosure, a method of endomechanical suturing a prolapsed organ within a pelvic cavity of a patient is disclosed. The method steps comprises: accessing the pelvic cavity of the patient; identifying the prolapsed organ within the pelvic cavity; positioning the prolapsed organ proximate to a human tissue; and suturing, via a suturing device, the prolapsed organ to the human tissue to suspend the prolapsed organ within the pelvic cavity.

In accordance with another aspect of the disclosure, a method for performing sacrocolpopexy surgery for a prolapsed organ is disclosed. The method comprises: accessing a pelvic cavity of a patient; identifying the prolapsed organ within the pelvic cavity; preparing a first attachment site on the side of the prolapsed organ; preparing a second attachment site on a sacrum; inserting a mesh material into the pelvic cavity, extending from the first attachment site to the second attachment site; suturing, via a suturing device, the mesh material at the first attachment site on the side of the prolapsed organ; and suturing, via the suturing device, the mesh material to the sacrum at the second attachment site to suspend the prolapsed organ within the pelvic cavity.

These and other aspects and features of the present disclosure will be better understood upon reading the following detailed description when read in conjunction with the accompanying drawings.

BRIEF DESCRIPTION OF THE DRAWINGS

FIG. 6 is a flow-chart of a method of suturing a prosthetic to human tissue, according to an embodiment of the present disclosure.

FIG. 8 is a flow-chart of a method for performing sacrocolpopexy surgery for a prolapsed organ, according to another embodiment of the present disclosure.

Figure 1:
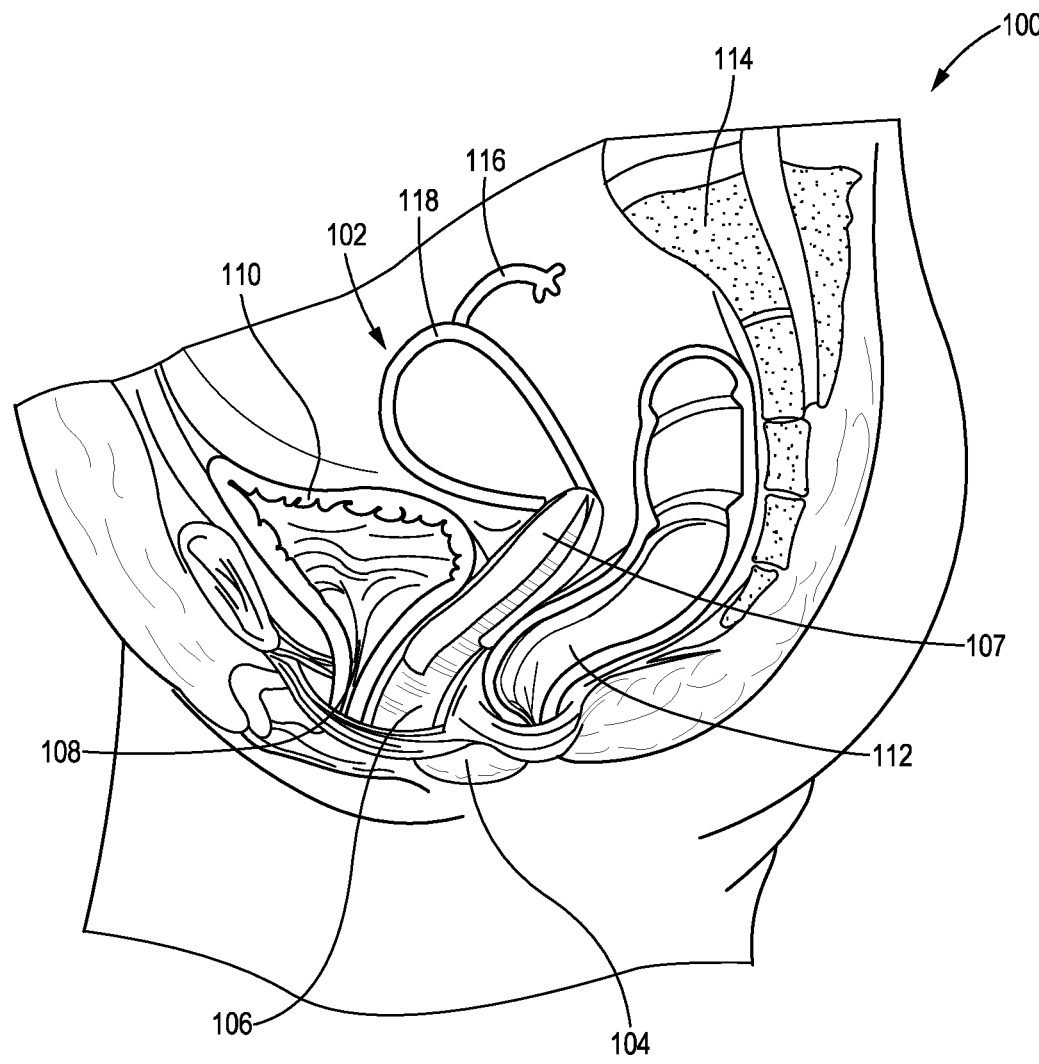
FIG. 1 is a cross-sectional view of a pelvic cavity of a female human, according to an embodiment of the present disclosure.

The figures depict one embodiment of the presented disclosure for purposes of illustration only. One skilled in the art will readily recognize from the following discussion that alternative embodiments of the structures and methods illustrated herein may be employed without departing from the principles described herein.

DETAILED DESCRIPTION

Referring now to the drawings, and with specific reference to the depicted example, a body portion 100 of a human body is shown, illustrated as a pelvic cavity 102 of a female human. While the following detailed description describes an exemplary aspect in connection with performing sacrocolpopexy surgery, it should be appreciated that the description applies equally to the use of the present disclosure in other surgeries, including, but not limited to, endomechanical suturing and in-situ suturing of other prosthetics to human tissues and organs as well.

Referring now to FIG. 1, a cross-section of the pelvic cavity 102 of a female human is illustrated, according to one embodiment of the disclosure. The pelvic cavity 102 comprises a pelvic floor 104 supporting a vagina 106, a urethra 108, a bladder 110, a rectum 112, a sacrum 114, a fallopian tube 116, a uterus 118, and other muscles, ligaments, and organs, as generally known in a female body (collectively, referred herein as "Pelvic Organs").

The pelvic floor 104 is a group of muscles, ligaments, and connective tissues that provide support to the pelvic organs within the pelvic cavity 102 for proper position and functioning of the Pelvic Organs. The pelvic floor 104 provides support in: (1) maintaining bladder control by providing support and preventing the descent or prolapse of the bladder 110; (2) preventing descent or prolapse of the uterus 118; (3) maintaining proper functioning of the rectum 112 and prevent its descent or prolapse for normal bowel control and the normal passage of stool; (4) supporting the vagina 106 for contributing to sexual function, and aiding in childbirth. The strength and integrity of the pelvic floor 104 is crucial for maintaining optimal support and function of the Pelvic Organs. In cases of pelvic organ prolapse, one or more of the Pelvic Organs may descend or protrude due to weakened or damaged supporting structures, ligaments, tissues, and/or muscles, such as a weakening or damaged pelvic floor 104.

Figure 2:
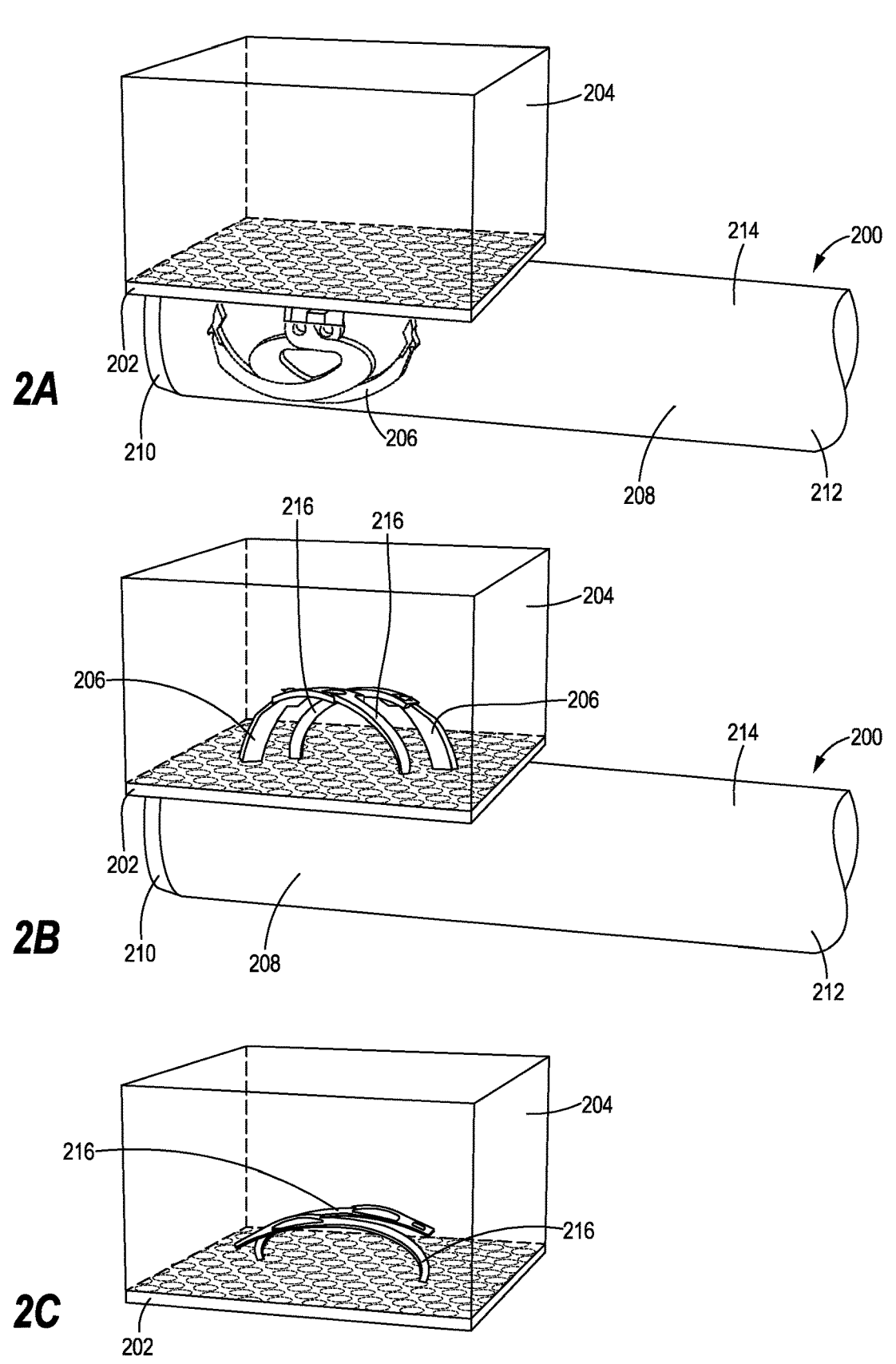
FIG. 2 is a perspective view of a sequence of suturing a prosthetic to a human tissue with a surgical tool, according to one embodiment of the present disclosure.

Now referring to FIG. 2, a perspective view of a sequence of suturing a prosthetic 202 to a human tissue 204 with a surgical tool 200 is illustrated, according to one embodiment of the disclosure. The surgical tool 200, illustrated as a portion of a suturing device, may be endomechanically positioned proximate to the human tissue 204, as shown in 2A. One may recognize that the human tissue 204 may be a portion of a ligament or organ of a human body. The prosthetic 202 may be provided as a mesh material and positioned between the surgical tool 200 and the human tissue 204.

The surgical tool 200 may be aligned proximate to the human tissue 204 with the prosthetic 202. The surgical tool 200 may have an elongated member 208 with a distal end 210, a proximal end 212, and a lateral side 214 therebetween. The surgical tool 200 may include a plurality of sutures, fasteners, and/or staples, as generally known in the arts. For example, the distal end 210 may be aligned with the prosthetic 202 on a side of the vagina 106 along a vaginal wall 107. The surgical tool 200 may include deployment members 206 which deploy a plurality of surgical fasteners, such as surgical sutures, needles, and staples, to fixate the mesh material to the human tissue 204.

The surgical tool 200 may be a suturing device such as a suture passer, an endoscopic suturing device, a robotic suturing device, or another similar suturing device configured to suture human tissue 204, as generally known in the arts. Two examples are disclosed in U.S. Pat. Nos. 10,492, 778 and 9,603,592 which are hereby incorporated by reference in both of their entirety.

As shown in FIG. 2B, the surgical tool 200 may be actuated for in-situ suturing to drive the deployment members 206 of the surgical tool 200 outwardly away from the lateral side 214, through the prosthetic 202 and into the human tissue 204 of one of the Pelvic Organs for deploying a plurality of surgical fasteners 216 to fasten the prosthetic 202 to the human tissue 204. The surgical tool 200 may be further configured to retract the deployment members 206 back into the lateral side 214 of the surgical tool 200 while subsequently deploying the plurality of surgical fasteners 216 to fasten the prosthetic 202 to the human tissue 204. As shown in FIG. 2C, the surgical tool 200 is removed after the plurality of surgical fasteners 216 have been deployed by the surgical tool 200 and the prosthetic 202 is securely fastened to the human tissue 204. The plurality of surgical fasteners 216 remain in the human tissue 204, such as the vaginal wall 107, after the plurality of deployment members 206 are retracted and the surgical tool 200 is removed. For example, a plurality of sutures may remain, whereby the sutures fasten the human tissue 204 to a prosthetic 202 or another tissue, ligament, or organ in the pelvic cavity 102.

Figure 3:
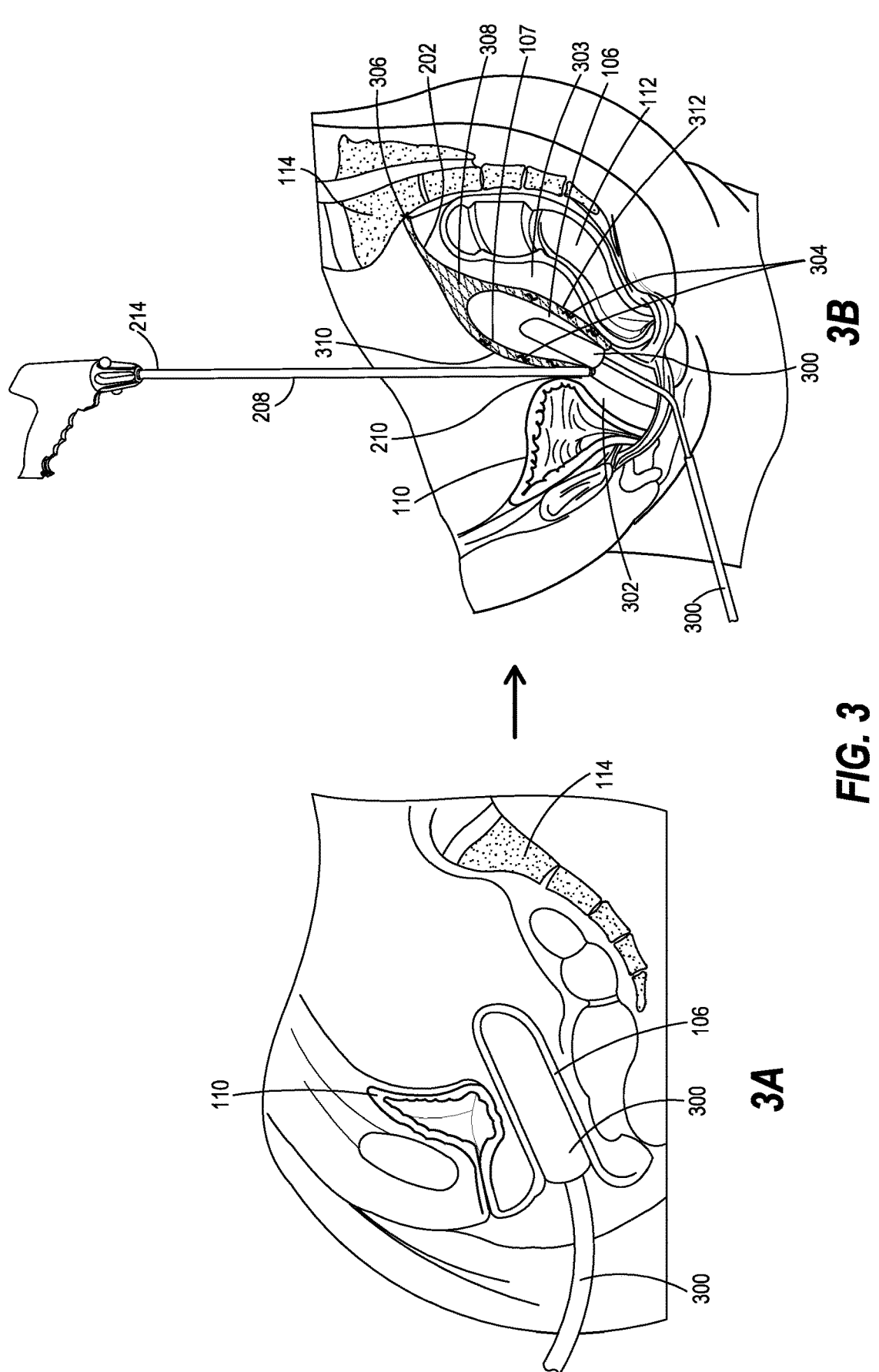
FIG. 3 is a cross-sectional illustration of performing a sequence of suspending a prolapsed organ in the pelvic cavity of FIG. 1, according to an embodiment of the present disclosure.

FIG. 3 is a cross-sectional illustration of performing a sequence of suspending a prolapsed organ in the pelvic cavity 102 of FIG. 1, according to an embodiment of the present disclosure. As shown in FIG. 3A, an obturator 300 is inserted into the vagina 106 for the purpose of repositioning the vagina 106 for facilitating: (1) dissection of opening spaces for the vagina 106 between both the bladder 110 and rectum 112 to provide access to the surgical tool 200 for suturing the vagina 106; and (2) matching a side angle of the vaginal wall 107 with a mesh material 308 for proper and secure suturing of the mesh material 308 to the vaginal wall 107. The obturator 300 is a uterine manipulator, as generally known in the arts. The obturator 300 may be used for laparoscopic vaginal prolapse repair procedures where the cervix has been removed and used for laparoscopic vaginal prolapse repair procedures where the cervix is intact, as generally known in the arts to support sacrocolpopexy surgeries.

As shown in FIG. 3B, the obturator 300 may lift the vagina 106 and facilitate dissection of a vesicovaginal space 302 between the vagina 106 and the bladder 110, as a well as a rectovaginal space 303 between the rectum 112 and the vagina 106. The vesicovaginal space 302 allows for the surgical tool 200 to reach the vagina 106 at a first attachment site 304 to secure an anterior leaf 310 of the mesh material 308 to the vaginal wall 107 of the vagina 106. The vesico- vaginal space 302 facilitates matching the anterior leaf 310 of the mesh material 308 with a side angle of the vaginal wall 107 for a proper suturing and a secure fixation of the mesh material 308 to the vaginal wall 107 with the plurality of surgical fasteners 216. The rectovaginal space 303 allows for the surgical tool 200 to reach the vaginal wall 107 and secure a posterior leaf 312 of the mesh material 308 to the vaginal wall 107. The rectovaginal space 303 facilitates matching the posterior leaf 312 of the mesh material 308 with a side angle of the vaginal wall 107 for a proper suturing and a secure fixation of the mesh material 308 to the vaginal wall 107 with the plurality of surgical fasteners 216.

The surgical tool 200, illustrated as a suturing device, may be endomechanically positioned proximate to the vagina 106, which may be identified as a prolapsed organ requiring suspension in the pelvic cavity 102. The surgical tool 200 may include surgical sutures, fasteners, and/or staples for deployment, as generally known in the arts. For example, the distal end 210 may be aligned with the prosthetic 202 on a side of the vagina 106 along the vaginal wall 107. The surgical tool 200 may be provided to conduct side suturing of the prosthetic 202 to the human tissue 204 or Pelvic Organs.

The surgical tool 200 may be actuated for in-situ suturing to drive deployment members 206 of the surgical tool 200 outwardly away from the lateral side 214, through the prosthetic 202 and into one of the Pelvic Organs at the first attachment site 304 and/or the second attachment site 306. The surgical tool 200 may be further configured to retract the deployment members 206 back into the lateral side 214 of the surgical tool 200 leaving the prosthetic 202 fastened, by the plurality of surgical fasteners 216, to be suspended from the human tissue 204 and/or Pelvic Organs. The plurality of surgical fasteners 216, such as a suture, remain in the human tissue 204 and/or Pelvic Organs, such as the vaginal wall 107, after the plurality of deployment members 206 are retracted. The prosthetic 202 may be further secured at a second attachment site 306 near the sacrum 114 to support lifting the prolapsed vagina 106 to be suspended within the pelvic cavity 102.

The prosthetic 202 may be a mesh material 308 used in surgical procedures for prolapsed organs and made of syn- thetic materials such as polypropylene, polyethylene tere- phthalate (PET), polyvinylidene fluoride (PVDF), polyester, and polyethylene. The mesh material 308 may be positioned between the surgical tool 200 and the human tissue 204 of a prolapsed organ. The prosthetic 202 may allow for long- term support and reinforcement of the weakened or damaged tissues as well as reducing risk of complications such as infection or rejection. The mesh material 308 may be sutured endomechanically, using in-situ suturing techniques, to the vaginal wall 107 on a side of the vagina 106. The mesh material 308 may be further sutured endomechanically, using in-situ suturing techniques. The mesh material 308 may be sutured endomechanically, using in-situ suturing techniques, to the vaginal wall 107 on a side of the vagina 106 at the first attachment site 304.

The mesh material 308 may be further sutured endome- chanically or by traditional surgical suturing methods, using in-situ suturing techniques, to extend the prosthetic 202 to the sacrum 114 at the second attachment site 306 to lift the vagina 106 in the pelvic cavity 102. A surgeon may first secure the prosthetic 202 to a Pelvic Organ, subsequently followed by suturing an opposite end of the prosthetic 202 to the sacrum 114.

Figure 4:
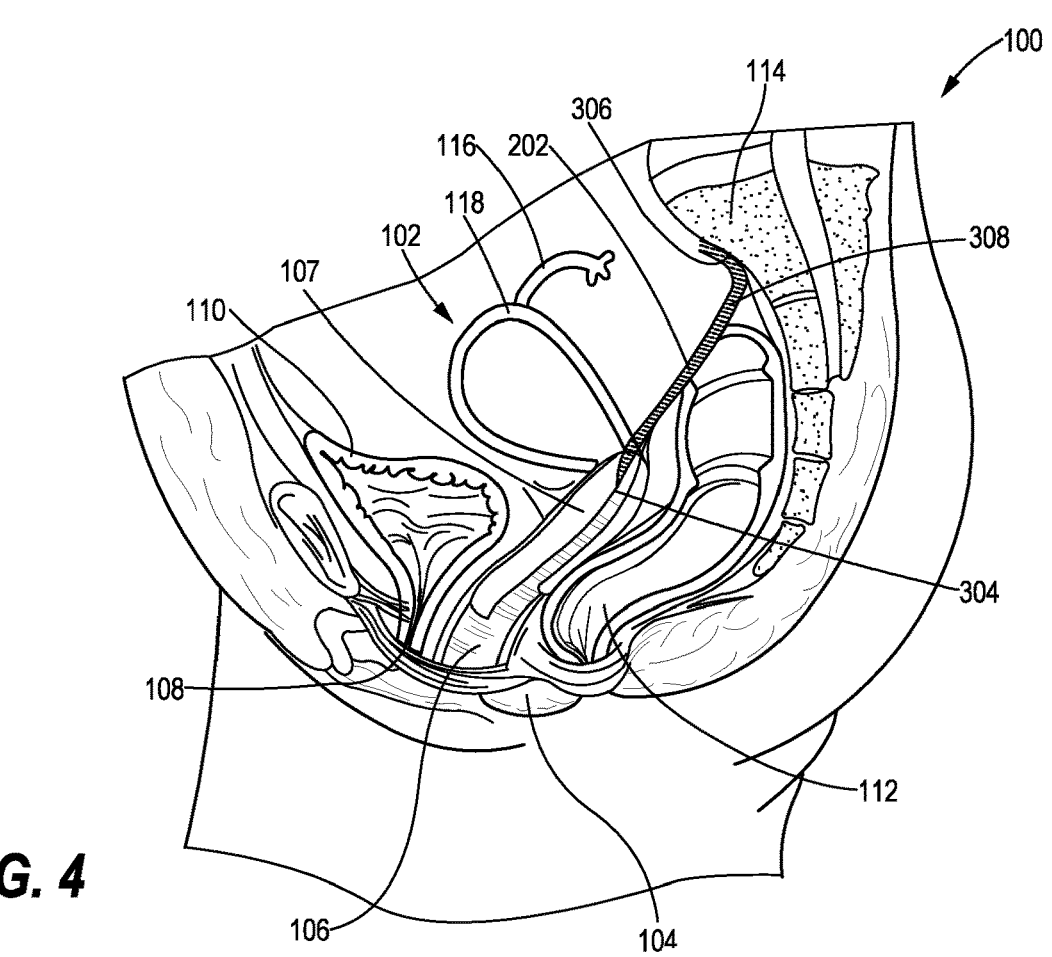
FIG. 4 is a cross-sectional view of the pelvic cavity of FIG. 1 with a prosthetic suspending a prolapsed organ in the pelvic cavity of FIG. 1, according to an embodiment of the present disclosure.

Now referring to FIG. 4, a cross-sectional view of the pelvic cavity 102 of FIG. 1 with the prosthetic 202 suspend- ing a prolapsed organ in the pelvic cavity 102 is illustrated, according to an embodiment of the present disclosure. The prosthetic 202 is provided as mesh material 308 extending from the first attachment site 304 on the vagina 106 to the second attachment site 306 along the sacrum 114 for sus- pending the vagina 106 in the pelvic cavity 102.

Figure 5:
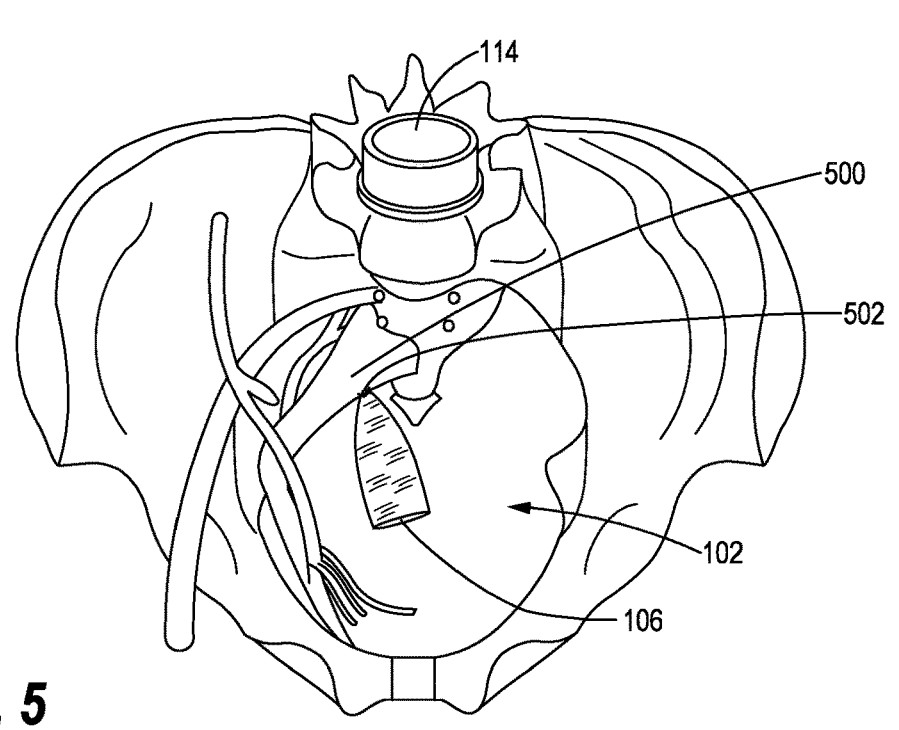
FIG. 5 is a cross-sectional top view of the pelvic cavity of FIG. 1 with a prolapsed organ suspended in the pelvic cavity, according to another embodiment of the present disclosure.

Now referring to FIG. 5, is a cross-sectional top view of the pelvic cavity of FIG. 1 with a prolapsed organ suspended in the pelvic cavity 102, according to another embodiment of the present disclosure. The vagina 106, in a prolapsed condition, may be lifted using the obturator 300 to reach a sacrospinous ligament 500, securing the vagina 106 to a ligament attachment site 502 on the sacrospinous ligament 500, a bi-lateral structure in the pelvic cavity 102. Securing the vagina 106 to the human tissue 204, such as the sacrospinous ligament 500, does not require the prosthetic 202 because the sacrospinous ligament 500 suspends the vagina 106 from a prolapsed condition in the pelvic cavity 102. The vagina 106 may be fixated or secured to be suspended to the sacrospinous ligament 500 by one or more of the plurality of surgical fasteners 216 deployed by the plurality of deployment members 206 of the surgical tool 200.

INDUSTRIAL APPLICABILITY

In operation, the present disclosure may find applicability in many industries including, but not limited to, the medical industries. Specifically, the methods of the present disclo- sure may be used for performing gynecology surgeries, and, more particularly, sacrocolpopexy surgery. While the fore- going detailed description is made with specific reference to sacrocolpopexy surgery, it is to be understood that its teachings may also be applied onto other non-invasive or minimally invasive surgeries requiring prosthetics including but not limited to sacrocolpopexy, rectopexy, and other pexy-like surgeries in which organs are suspended into a non-prolapsed state.

Now referring to FIG. 6, a method 600 of suturing the prosthetic 202 to human tissue 204 is illustrated, according to one embodiment of the disclosure. In a step 602, a surgical site on the body portion 100 of a patient is accessed. The surgical site may be accessed through a laparoscopic, endomechanically, or through an open abdominal approach. In a step 604, the human tissue 204 within the surgical site is identified for suturing the prosthetic 202. The suturing may be performed using in-situ suturing techniques. The suturing may be performed on a side of the human tissue 204 or a side of one of the Pelvic Organs.

In a step 606, the prosthetic 202 is endomechanically positioned adjacent the human tissue 204 or prolapsed organ within the surgical site. In a step 608, the surgical tool 200 is aligned proximate the human tissue 204 with the pros- thetic 202 between the surgical tool 200 and the human tissue 204. In a step 610, the surgical tool 200 is actuated in-situ to drive the plurality of deployment members 206 of the surgical tool 200 outwardly away from surgical tool 200 or, more specifically, the lateral side 214, through the prosthetic 202 and into the human tissue 204.

In endomechanical suturing, the sutures are typically preloaded into the suturing device, eliminating the need for the surgeon to handle individual needles. The suturing device may consist of a needle holder, suture passer, or other instruments specifically designed for intraoperative suturing. In-situ suturing techniques may be conducted by endomechanical suturing with the suturing device. the plurality of deployment members 206 may be deployed when actuated the surgical tool 200 providing for multiple sutures, fasteners, and/or needles through the prosthetic 202 and into the human tissue 204.

In a step 612, the plurality of deployment members 206 are retracted back into the lateral side 214 of the surgical tool 200 leaving the prosthetic 202 fixated to the human tissue 204 by a deployed fastener. When retracting the deployment members back into the surgical tool 200, the deployment members deploy a surgical fastener to fixatedly suspend the prosthetic 202 to one of the Pelvic Organs. The deployment members 206 may deploy the plurality of surgical fasteners 216, a plurality of surgical sutures, a plurality of surgical screws, and the like. In a step 614, the surgical site is closed upon completion of surgery. In some embodiments or surgeries, if the diameter of the surgical tool 200 is small enough, e.g. having an 8 mm or less cross-sectional diameter, the surgical site may not need to be closed.

Figure 7:
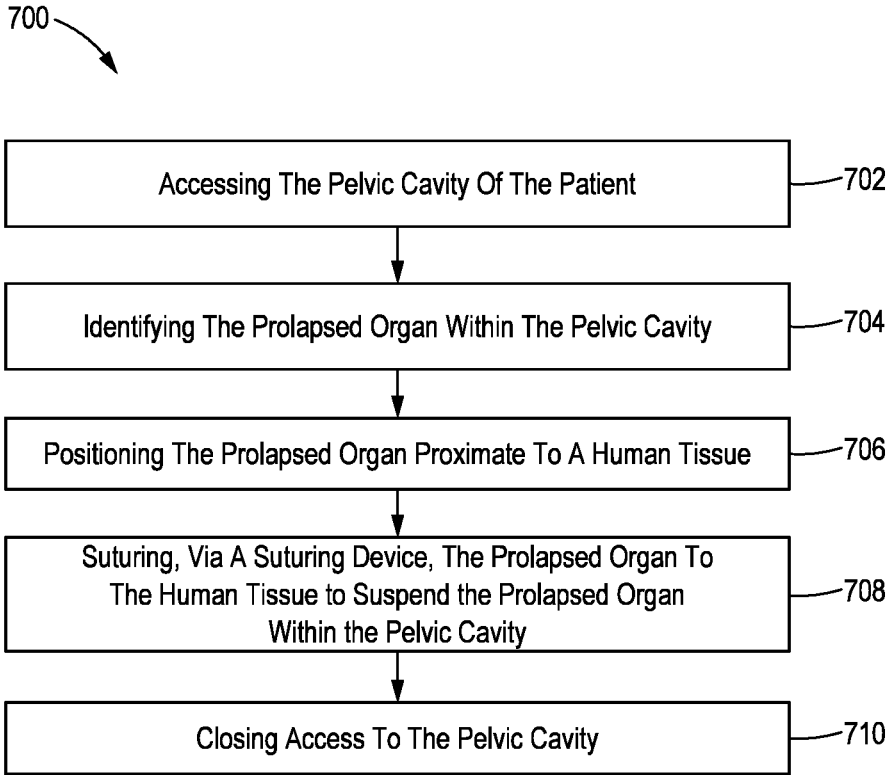
FIG. 7 is a flow-chart of a method of endomechanical suturing of a mesh material to a prolapsed organ within a pelvic cavity of a patient, according to another embodiment of the present disclosure.

Now referring to FIG. 7, a method 700 of endomechanical suturing of a mesh material 308 to a prolapsed organ within the pelvic cavity 102 is illustrated, according to another embodiment of the disclosure. In a step 702, the pelvic cavity 102 on the body portion 100 is accessed. The pelvic cavity 102 may be accessed through a laparoscopic or open abdominal approach. In a step 704, the prolapsed organ within the pelvic cavity 102 is identified for endomechanical suturing of the mesh material 308.

In a step 706, the prolapsed organ is positioned proximately to the human tissue 204 such as the sacrospinous ligament 500 using the obturator 300 as a uterine manipulator, as generally known in the arts for laparoscopic vaginal prolapse repair procedures. In a step 708, the prolapsed organ is sutured, via a suturing device, at the ligament attachment site 502 to human tissue 204 in the pelvic cavity 102 to suspend the prolapsed organ within the pelvic cavity 102 directly supported by human tissue 204 such as the sacrospinous ligament 500. In a step 710, access to the pelvic cavity 102 is closed upon completion of the suturing and surgery by the surgeon.

In another embodiment, the prosthetic 202 may be provided as a mesh material 308 and inserted into the pelvic cavity 102 between the prolapsed organ and the sacrospinous ligament 500. Thus, in step 708, the prosthetic 202 may extend from the first attachment site 304 on the prolapsed organ to the second attachment site 306 on the human tissue 204 to suspend the prolapsed organ within the pelvic cavity 102. The first attachment site 304 may be prepared on the side of the prolapsed organ, such as the vagina 106 along the vaginal wall 107, and the second attachment site 306 may be prepared on human tissue 204 within the pelvic cavity 102, such as on the sacrum 114.

The mesh material 308 may also be sutured on the prolapsed organ at the first attachment site 304 via a suturing device. The mesh material 308 is sutured to the sacrum 114 inside the pelvic cavity 102 to suspend the prolapsed organ within the pelvic cavity 102. The mesh material 308 may be endomechanical sutured on a side of the prolapsed organ. In step 708, a plurality of surgical sutures, surgical fasteners, and/or surgical needles provided in the suturing device may be deployed when actuated the suturing device, whereby one or more sutures, fasteners, and/or needles are provided through the prosthetic 202 and into the prolapsed organ.

Now referring to FIG. 8, a method 800 for performing sacrocolpopexy surgery for a prolapsed organ is illustrated, according to another embodiment of the disclosure. In a step 802, the pelvic cavity 102 on the body portion 100 is accessed through a laparoscopic or open abdominal surgical approach. In a step 804, the prolapsed organ within the pelvic cavity 102 is identified.

In a step 806, the prosthetic 202, provided as a mesh material 308, is inserted into the pelvic cavity 102, extending from the first attachment site 304 to the second attachment site 306 in the pelvic cavity 102 to suspend the prolapsed organ within the pelvic cavity 102. The first attachment site 304 may be prepared on the side of a prolapsed organ, such as the vagina 106 along the vaginal wall 107. The second attachment site 306 may be prepared on the sacrum 114.

In a step 808, the mesh material 308 is sutured on the prolapsed organ at the first attachment site 304 via a suturing device. The mesh material 308 may be sutured using in-situ suturing techniques endomechanically. The first attachment site 304 may be positioned on a side of the prolapsed organ when preparing to suture. In a step 810, the mesh material 308 is sutured, via the suturing device, to the second attachment site 306 inside the pelvic cavity 102 to suspend the prolapsed organ within the pelvic cavity 102, such as the vagina 106. In steps 808 and 810, a plurality of surgical sutures, surgical fasteners, and/or surgical needles provided in the suturing device may be deployed when actuated the suturing device, whereby one or more surgical sutures, surgical fasteners, and/or surgical needles are provided through the mesh material 308 and into the prolapsed organ. In a step 812, access to the pelvic cavity 102 is closed upon completion of the surgery by the surgeon.

In the event of vaginal prolapse, suspending the vagina 106 through side-endomechanical suturing of the mesh material 308 to the vaginal wall 107 extending to the sacrum 114 may alleviate symptoms associated with vaginal prolapse as well as aiding in restoring pelvic organ support, improving pelvic floor 104 functioning, and preventing further prolapse progression. Moreover, the side suturing method allows the surgeon better access and view of the prolapse, position the prosthetic 202 as necessary, and accurately suspend or otherwise attach the prosthetic 202 to the human tissue 204 with minimum obstruction or inability to see.

From the foregoing, it can be seen that the technology disclosed herein has industrial applicability in a variety of settings such as, but not limited to, the medical industry for performing surgeries involving suturing of prosthetics to human tissues and organs.

What is claimed is:

1. A method of securing a prosthetic to an organ, the method comprising of:

accessing a surgical site on a body portion of a patient;

identifying the organ within the surgical site;

endomechanically positioning the prosthetic adjacent the organ within the surgical site;

aligning a surgical tool proximate the organ with the prosthetic between the surgical tool and the organ, the surgical tool having an elongated member with distal and proximal ends;

actuating the surgical tool in-situ, to drive deployment members of the surgical tool outwardly away from the surgical tool, through the prosthetic and into the organ; and retracting the deployment members back into the surgical tool, whereby the deployment members deploy a surgical fastener to fixatedly suspend the prosthetic to the organ.

2. The method of claim 1, wherein accessing the surgical site of the patient includes performing a laparoscopic procedure or an open abdominal procedure.

3. The method of claim 1, wherein the organ may be chosen from a group consisting of a prolapsed uterus, a prolapsed bladder, a prolapsed rectum, prolapsed vagina, a prolapsed bowel, a prolapsed urethra, prolapsed fallopian tubes, and prolapsed ovaries.

4. The method of claim 1, wherein the surgical site is a pelvic cavity.

5. The method of claim 1, wherein the surgical tool may be chosen from a group consisting of a suture passer, an endoscopic suturing device, a robotic suturing device.

6. The method of claim 5, wherein the surgical fastener is one of a plurality of surgical sutures, a plurality of surgical fasteners, and a plurality of surgical staples.

7. The method of claim 1, wherein the prosthetic is a mesh material made of a polymeric mesh material selected from a group consisting of a polypropylene, a polyethylene terephthalate (PET), a polyvinylidene fluoride (PVDF), a polyester, and a polyethylene.

8. A method for performing sacrocolpopexy surgery for a prolapsed organ, the method steps comprising of:

accessing a pelvic cavity of a patient;

identifying the prolapsed organ within the pelvic cavity;

inserting a mesh material into the pelvic cavity, extending from a first attachment site on the prolapsed organ to a second attachment site within the pelvic cavity;

suturing, via a suturing device, the mesh material on the prolapsed organ, the suturing device drives deployment members in-situ and outwardly away from the surgical device, through the mesh material, into the first attachment site and back into the surgical device whereby the deployment members deploy a surgical fastener to fixatedly suspend the mesh material to the prolapsed organ; and suturing the mesh material to a human tissue at the second attachment site in the pelvic cavity to suspend the prolapsed organ within the pelvic cavity.

9. The method of claim 8, wherein accessing the pelvic cavity of the patient includes performing a laparoscopic procedure or an open abdominal procedure, and the method further includes:

inserting the suturing device into the pelvic cavity when suturing the mesh material to the first attachment site and the second attachment site.

10. The method of claim 8, wherein suturing, via the suturing device, the mesh material to the first attachment site and second attachment sites includes using one of: a plurality of surgical sutures, a plurality of fasteners, a plurality of screws, and a plurality of staples.

11. The method of claim 8, wherein the second attachment site is located on a sacrum or a human tissue wall proximate to the sacrum.

12. The method of claim 8, wherein:

the prolapsed organ may be chosen from a group consisting of a prolapsed uterus, a prolapsed bladder, a prolapsed rectum, a prolapsed vagina, a prolapsed bowel, a prolapsed urethra, prolapsed fallopian tubes, and prolapsed ovaries; and the mesh material comprises a polymeric mesh material selected from a group consisting of a polypropylene, a polyethylene terephthalate (PET), a polyvinylidene fluoride (PVDF), a polyester, and a polyethylene.

13. The method of claim 8, wherein the suturing device may be chosen from a group consisting of a suture passer, an endoscopic suturing device, a robotic suturing device, and wherein the suturing device is configured to include at least one of the following: an automated suture deployment feature, and an adjustable suture tension feature for accurate and consistent suturing.

14. The method of claim 13, wherein the first attachment site is on a side of the prolapsed organ.

* * * * *